United States Patent
Jang et al.

(10) Patent No.: US 11,439,475 B2
(45) Date of Patent: Sep. 13, 2022

(54) DRUG DELIVERY ROBOT

(71) Applicant: IUCF-HYU (INDUSTRY-UNIVERSITY COOPERATION FOUNDATION HANYANG UNIVERSITY), Seoul (KR)

(72) Inventors: Gunhee Jang, Seoul (KR); Jae Kwang Nam, Goyang-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 442 days.

(21) Appl. No.: 16/626,042

(22) PCT Filed: Jun. 18, 2018

(86) PCT No.: PCT/KR2018/006839
§ 371 (c)(1),
(2) Date: Dec. 23, 2019

(87) PCT Pub. No.: WO2018/236104
PCT Pub. Date: Dec. 27, 2018

(65) Prior Publication Data
US 2021/0137622 A1    May 13, 2021

(30) Foreign Application Priority Data

Jun. 21, 2017  (KR) .................. 10-2017-0078328

(51) Int. Cl.
*A61B 34/30*        (2016.01)
*A61B 34/00*        (2016.01)
*A61B 17/16*        (2006.01)

(52) U.S. Cl.
CPC .......... *A61B 34/73* (2016.02); *A61B 17/1615* (2013.01); *A61B 34/30* (2016.02); *A61B 2034/731* (2016.02)

(58) Field of Classification Search
CPC .......... A61B 17/1617; A61B 2034/731; A61B 34/73; A61B 17/1615; A61B 34/30;
(Continued)

(56) References Cited

U.S. PATENT DOCUMENTS 6,537,232 B1    3/2003  Kucharczyk et al.
2005/0085696 A1  4/2005  Uchiyama et al.
(Continued)

FOREIGN PATENT DOCUMENTS

JP    3008264 B2    2/2000
JP    2007-151729 A  6/2007
(Continued)

OTHER PUBLICATIONS

International Search Report of PCT/KR2018/006839 dated Sep. 20, 2018.

*Primary Examiner* — Samuel S Hanna
(74) *Attorney, Agent, or Firm* — Sughrue Mion, PLLC

(57) ABSTRACT

A drug delivery robot is provided. The drug delivery robot comprises: a storage space in which a drug is stored; a first accommodation unit formed at the front of the storage space along a first direction; an outlet by which the first accommodation unit communicates with the outside; a body having a first communication hole by which the storage space communicates with the first accommodation unit; a front rotational magnet which is located in the first accommodation unit and has a central axis arranged in a second direction perpendicular to the first direction; a first fixed magnet which is fixedly coupled to one side of the body in the rear of the front rotational magnet; and a second fixed magnet which is fixedly coupled to the other side of the body while having the storage space between the first fixed magnet and the second magnet and is arranged to face polarities different (Continued)

from those of the first fixed magnet, wherein the front rotational magnet can selectively rotate around an axis of the first direction or the second direction by means of an external magnetic field control, the body rotates together around the axis of the first direction when the front rotational magnet rotates around the axis of the first direction, the front rotational magnet opens or closes the first communication hole by means of the magnetic force with the first fixed magnet and the second fixed magnet when the front rotational magnet rotates around the axis of the second direction.

11 Claims, 6 Drawing Sheets

(58) Field of Classification Search
CPC ............ A61M 25/0127; A61M 31/002; A61M 25/01; A61M 25/0116; A61M 25/0125; A61M 31/00; A61M 37/00; A61K 9/50
See application file for complete search history.

(56) References Cited

U.S. PATENT DOCUMENTS

| | | |
|---|---|---|
| 2008/0255543 A1 | 10/2008 | Tanaka et al. |
| 2010/0001592 A1 | 1/2010 | Kawano et al. |
| 2014/0163664 A1 | 6/2014 | Goldsmith |
| 2015/0045658 A1 | 2/2015 | Tange et al. |
| 2017/0071622 A1* | 3/2017 | Jang ................ A61B 34/30 |

FOREIGN PATENT DOCUMENTS

| | | |
|---|---|---|
| JP | 2013-537081 A | 9/2013 |
| KR | 10-2010-0015207 A | 2/2010 |
| KR | 10-2010-0026438 A | 3/2010 |
| KR | 10-2014-0026957 A | 3/2014 |
| KR | 10-1458938 B1 | 11/2014 |
| KR | 10-1471526 B1 | 12/2014 |
| KR | 10-1543708 B1 | 8/2015 |
| KR | 10-1642022 B1 | 7/2016 |

* cited by examiner (a)

(b)

DRUG DELIVERY ROBOT

CROSS REFERENCE TO RELATED APPLICATIONS

This application is a National Stage of International Application No. PCT/KR2018/006839 filed Jun. 18, 2018, claiming priority based on Korean Patent Application No. 10-2017-0078328 filed Jun. 21, 2017.

TECHNICAL FIELD

The present invention relates to a drug delivery robot, and more particularly, to a drug delivery robot capable of moving and performing drug delivery under the control of an external magnetic field.

BACKGROUND ART

A magnetic robot may be inserted into a human body to perform medical activities. In particular, the magnetic robot has a small size, so that the magnetic robot may easily perform medical activities on a region where it is difficult for a doctor to directly perform a procedure, such as diagnosing a disease while moving inside the human body, or delivering a drug.

In general, when the magnetic robot is used for the purposed of drug delivery, the magnetic robot may be used to treat lesions inside the human body or to assist the drilling for perforating through a blockage in an organ such as a blood vessel, a small intestine, or a large intestine so that the drilling may be performed more smoothly.

However, a conventional magnetic robot for drug delivery has problems in that the drug may leak because it is difficult to completely seal a nozzle for delivering the drug, or precise drug delivery may be difficult because it is not easy to stop the movement and deliver the drug in place.

Accordingly, there is a demand for technologies for medical magnetic robots capable of preventing drugs from leaking and precisely performing drug delivery at a desired region.

DISCLOSURE

Technical Problem

A technical object of the present invention is to provide a drug delivery robot capable of moving along tubular organs in a human body and performing drug delivery under a control of an external magnetic field.

The technical objects of the present invention are not limited to the above-described objects.

Technical Solution

In order to achieve the technical objects, the present invention provides a drug delivery robot.

In accordance with one embodiment of the present invention, the drug delivery robot includes: a body including a storage space in which a drug is stored, a first accommodation portion formed at a front of the storage space in a first direction, an outlet which allows the first accommodation portion to communicate with an outside, and a first communication hole which allows the storage space to communicate with the first accommodation portion; a front rotational magnet located in the first accommodation portion and having a central axis arranged in a second direction perpendicular to the first direction; a first fixed magnet fixedly coupled to one side of the body at a rear of the front rotational magnet; and a second fixed magnet fixedly coupled to an opposite side of the body with the storage space interposed between the first fixed magnet and the second fixed magnet, and arranged such that mutually different polarities of the first and second fixed magnets face each other, wherein the front rotational magnet is able to selectively rotate about an axis in one of the first direction and the second direction under a control of an external magnetic field, the body rotates together with the front rotational magnet about the axis in the first direction when the front rotational magnet rotates about the axis in the first direction, and the front rotational magnet opens or closes the first communication hole by a magnetic force in association with the first fixed magnet and the second fixed magnet when the front rotational magnet rotates about the axis in the second direction.

According to one embodiment, the front rotational magnet may have a cylindrical shape, and may have an N-pole and an S-pole making contact with each other with the central axis interposed therebetween.

According to one embodiment, the first fixed magnet may apply a magnetic force to one of the N-pole and the S-pole of the front rotational magnet, and the second fixed magnet may apply a magnetic force to a remaining one of the N-pole and the S-pole of the front rotational magnet.

According to one embodiment, the rotation of the front rotational magnet about the axis in the first direction may be limited while the front rotational magnet may be freely rotatable about the axis in the second direction within the first accommodation portion.

According to one embodiment, an inner diameter of the first accommodation portion may be larger than an outer diameter of the front rotational magnet.

According to one embodiment, the body may be provided along an outer circumferential surface thereof with a protrusion having a spiral shape.

According to one embodiment, the body may include a second accommodation portion formed at a rear of the storage space in the first direction, an inlet which allows the second accommodation portion to communicate with the outside, and a second communication hole which allows the storage space to communicate with the second accommodation portion, the drug delivery robot may further include: a rear rotational magnet located in the second accommodation portion and having a central axis arranged in the second direction perpendicular to the first direction; a third fixed magnet fixedly coupled to the one side of the body at a front of the rear rotational magnet; and a fourth fixed magnet fixedly coupled to the opposite side of the body with the storage space interposed between the third fixed magnet and the fourth fixed magnet, and arranged such that mutually different polarities of the third and fourth fixed magnets face each other, the rear rotational magnet may selectively rotate about the axis in one of the first direction and the second direction under the control of the external magnetic field, the body may rotate together with the rear rotational magnet about the axis in the first direction when the rear rotational magnet rotates about the axis in the first direction, and the rear rotational magnet may open or close the second communication hole by a magnetic force in association with the third fixed magnet and the fourth fixed magnet when the rear rotational magnet rotates about the axis in the second direction.

According to one embodiment, the rear rotational magnet may have a cylindrical shape, and may have an N-pole and an S-pole making contact with each other with the central axis interposed therebetween.

According to one embodiment, the third fixed magnet may apply a magnetic force to one of the N-pole and the S-pole of the rear rotational magnet, and the second fixed magnet may apply a magnetic force to a remaining one of the N-pole and the S-pole of the rear rotational magnet.

According to one embodiment, an inner diameter of the second accommodation portion may be larger than an outer diameter of the rear rotational magnet.

In accordance with one embodiment of the present invention, the drug delivery robot includes: a body including a storage space in which a drug is stored, a second accommodation portion formed at a rear of the storage space in a first direction, an inlet which allows the second accommodation portion to communicate with an outside, and a second communication hole which allows the storage space to communicate with the second accommodation portion; a rear rotational magnet located in the second accommodation portion and having a central axis arranged in a second direction perpendicular to the first direction; a third fixed magnet fixedly coupled to one side of the body at a front of the rear rotational magnet; and a fourth fixed magnet fixedly coupled to an opposite side of the body with the storage space interposed between the third fixed magnet and the fourth fixed magnet, and arranged such that mutually different polarities of the third and fourth fixed magnets face each other, wherein the rear rotational magnet is able to selectively rotate about an axis in one of the first direction and the second direction under a control of an external magnetic field, the body rotates together with the rear rotational magnet about the axis in the first direction when the rear rotational magnet rotates about the axis in the first direction, and the rear rotational magnet opens or closes the second communication hole by a magnetic force in association with the third fixed magnet and the fourth fixed magnet when the rear rotational magnet rotates about the axis in the second direction.

Advantageous Effects

The drug delivery robot according to the embodiment of the present invention may move and perform the drilling while rotating about an axis in the first direction. While the drug delivery robot is moving, the front rotational magnet and the rear rotational magnet close the communication hole by magnetic forces of the fixed magnets, so that the drug in the storage space can be prevented from leaking to the outside.

In addition, in the drug delivery robot according to the embodiment of the present invention, as the front rotational magnet and the rear rotational magnet rotate about the axis in the second direction, the drug stored in the body can be precisely discharged to the outside. The discharged drug softens a stenosis portion in the tubular organs, and the stenosis portion can be easily perforated by performing the drilling of the drug delivery robot.

BEST MODE

Figure 1:
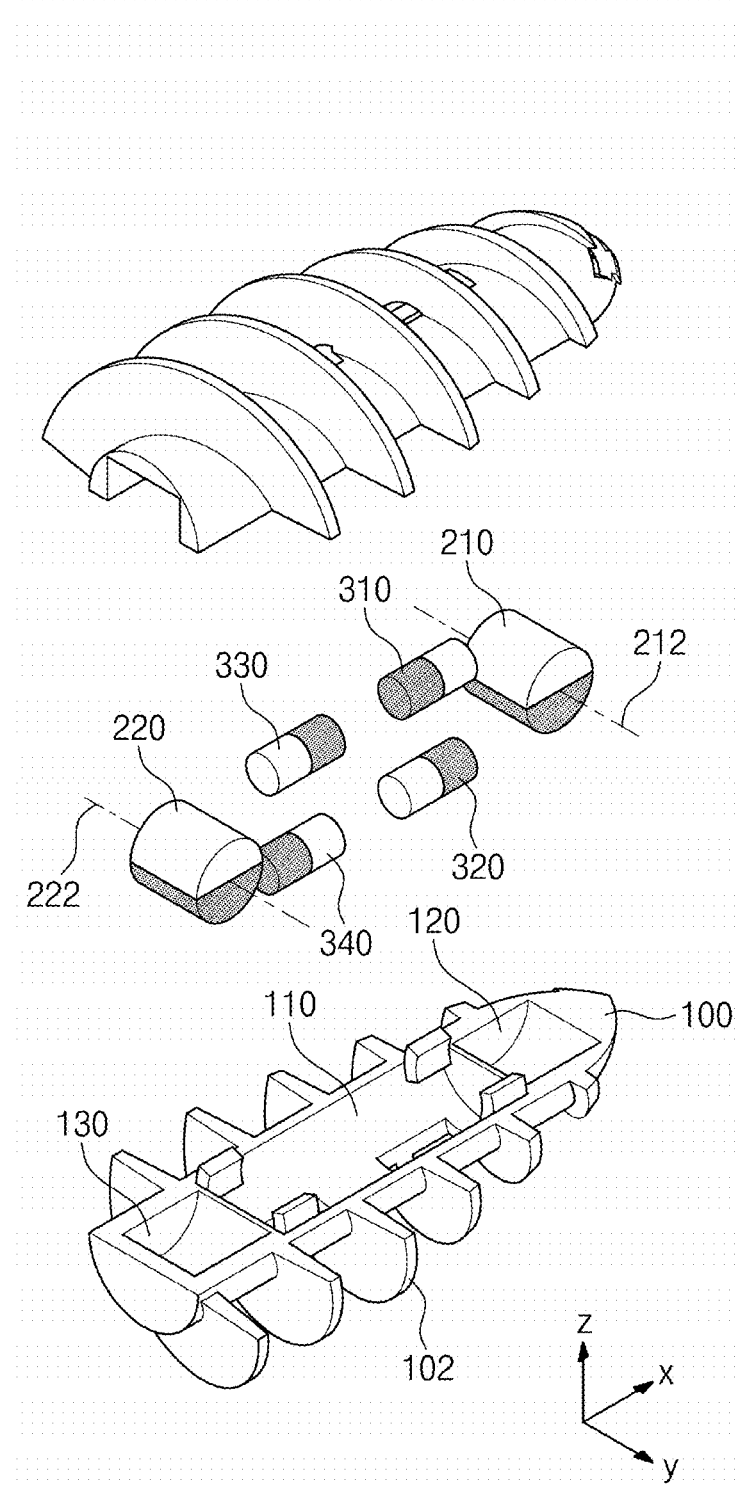
FIG. 1 is an exploded perspective view showing a drug delivery robot according to an embodiment of the present invention.

A drug delivery robot includes: a body including a storage space in which a drug is stored, a first accommodation portion formed at a front of the storage space in a first direction, an outlet which allows the first accommodation portion to communicate with an outside, and a first communication hole which allows the storage space to communicate with the first accommodation portion; a front rotational magnet located in the first accommodation portion and having a central axis arranged in a second direction perpendicular to the first direction; a first fixed magnet fixedly coupled to one side of the body at a rear of the front rotational magnet; and a second fixed magnet fixedly coupled to an opposite side of the body with the storage space interposed between the first fixed magnet and the second fixed magnet, and arranged such that mutually different polarities of the first and second fixed magnets face each other, wherein the front rotational magnet is able to selectively rotate about an axis in one of the first direction and the second direction under a control of an external magnetic field, the body rotates together with the front rotational magnet about the axis in the first direction when the front rotational magnet rotates about the axis in the first direction, and the front rotational magnet opens or closes the first communication hole by a magnetic force in association with the first fixed magnet and the second fixed magnet when the front rotational magnet rotates about the axis in the second direction.

Mode for Invention

Hereinafter, exemplary embodiments of the present invention will be described in detail with reference to the accompanying drawings. However, the technical idea of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the specification that one element is on another element, it means that a first element may be directly formed on a second element, or a third element may be interposed between the first element and the second element. Further, in the drawings, thicknesses of membranes and areas are exaggerated for efficient description of the technical contents.

In addition, in the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments described and illustrated herein include their complementary embodiments. Further, the team "and/or" in the specification is used to include at least one of the elements enumerated before and after the term.

In the specification, the terms of a singular form may include plural forms unless the context clearly indicates otherwise. Further, the terms such as "including" and "having" are used to designate the presence of features, numbers, steps, elements, or combinations thereof described in the specification, and shall not be construed to preclude any possibility of presence or addition of one or more other features, numbers, steps, elements, or combinations thereof.

Further, in the following description of the present invention, a detailed description of known functions and configurations incorporated herein will be omitted when it may make the subject matter of the present invention unnecessarily unclear.

Figure 2:
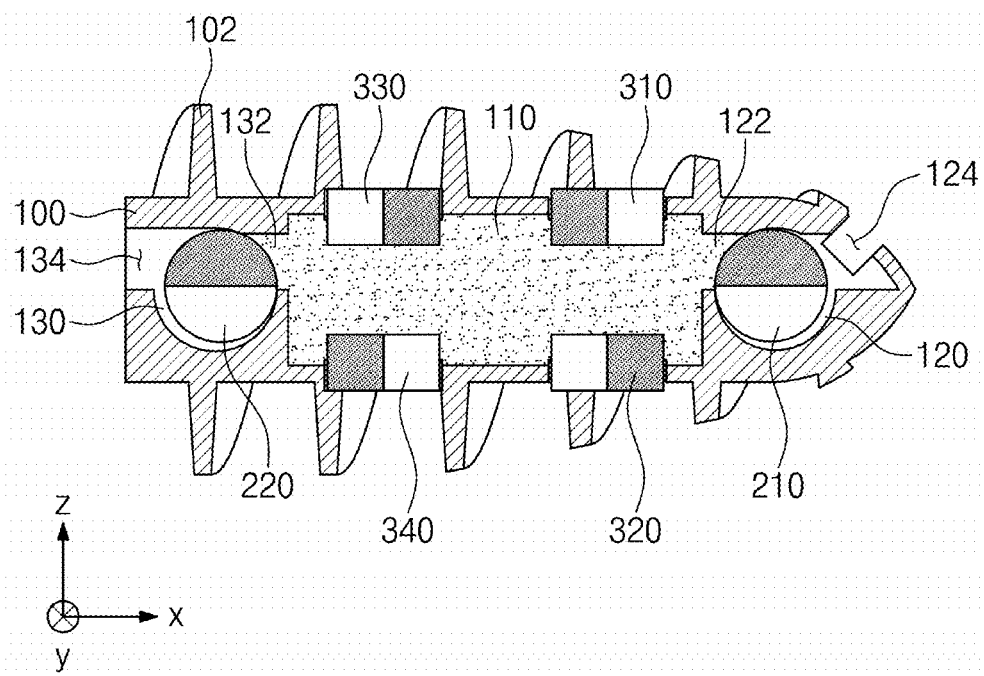
FIG. 2 is a sectional view showing the drug delivery robot according to the embodiment of the present invention.

FIG. 1 is an exploded perspective view showing a drug delivery robot according to an embodiment of the present invention, and FIG. 2 is a sectional view showing the drug delivery robot according to the embodiment of the present invention.

Referring to FIGS. 1 and 2, the drug delivery robot is movable along tubular organs of the human body, such as a blood vessel, a large intestine, or a small intestine, and may deliver a drug to soften a stenosis portion in the tubular organs and perform drilling to perforate a blocked portion. The drug delivery robot includes a body 100, a front rotational magnet 210, a rear rotational magnet 220, a first fixed magnet 310, a second fixed magnet 320, a third fixed magnet 330, and a fourth fixed magnet 340.

A plurality of magnets 210, 220, 310, 320, 330, and 340 may be provided such that an N-pole and an S-pole make contact with each other. In the drawing, the N-pole may be denoted by a darkened portion, and the S-pole may be denoted by a bright portion.

The body 100 may be provided therein with a storage space 110, a first accommodation portion 120, and a second accommodation portion 130. The second accommodation portion 130, the storage space 110, and the first accommodation portion 120 may be sequentially located from a rear end to a front end of the body 110. Hereinafter, a direction in which the second accommodation portion 130, the storage space 110, and the first accommodation portion 120 are sequentially located is referred to as a first direction x, and a direction perpendicular to the first direction x when viewed from the top is referred to as a second direction y. In addition, a direction perpendicular to the first direction x and the second direction y is referred to as a third direction z.

The storage space 110 is configured as a space in which the drug is stored, and the drug may be stored in the storage space 110 in the form of a liquid or solid. In addition, the drug may be stored in the form of a powder.

The first accommodation portion 120 may provide a space in which the front rotational magnet 210 is located. The first accommodation portion 120 may communicate with the storage space 110 through a first communication hole 122, and may communicate with an outside through an outlet 124 formed at the front end of the body 100. The drug stored in the storage space 110 may be supplied to the outside by sequentially passing through the first communication hole 122, the first accommodation portion 120, and the outlet 124.

The second accommodation portion 130 may provide a space in which the rear rotational magnet 220 is located. The second accommodation portion 130 may communicate with the storage space 110 through a second communication hole 132, and may communicate with the outside through an inlet 134 formed at the rear end of the body 100. A fluid staying outside the body 100 may be introduced into the second accommodation portion 130 through the inlet 134, and may be supplied into the storage space 110 through the second communication hole 132. When the drug delivery robot moves in a blood vessel, the fluid may be blood.

The front rotational magnet 210 may be located in the first accommodation portion 120. According to the embodiment, the front rotational magnet 210 may have a cylindrical shape, and may have a central axis 212 arranged in the second direction y. The front rotational magnet 210 may have the N-pole and the S-pole making contact with each other with the central axis 212 interposed therebetween.

An outer diameter of the front rotational magnet 210 may be smaller than an inner diameter of the first accommodation portion 120. In addition, a length of the front rotational magnet 210 in the second direction y may be longer than a height of the first accommodation portion 120 in the third direction z. Accordingly, the rotation of the front rotational magnet 210 about an axis in the first direction x may be limited while the front rotational magnet 210 may be freely rotatable about an axis in the second direction y within the first accommodation portion 120.

The front rotational magnet 210 may selectively rotate about an axis in one of the first direction x and the second direction y under the control of an external magnetic field.

For example, when the front rotational magnet 210 rotates about the axis in the first direction x, the body 100 may rotate together with the front rotational magnet 210 about the axis in the first direction x. In another example, when the front rotational magnet 210 rotates about the axis in the second direction y, the front rotational magnet 210 may open or close the first communication hole 122 by a magnetic force in association with the first fixed magnet 310 and the second fixed magnet 320. In detail, when an attractive force acts between the front rotational magnet 210 and the first and second fixed magnets 310 and 320, the front rotational magnet 210 may move toward the first and second fixed magnets 310 and 320, so that the first communication hole 122 may be closed by the front rotational magnet 210. Alternatively, when a repulsive force acts between the front rotational magnet 210 and the first and second fixed magnets 310 and 320, the front rotational magnet 210 may be pushed to an opposite side of the first and second fixed magnets 310 and 320, so that the first communication hole 122 may be opened. When the first communication hole 122 is opened by the front rotational magnet 210, the drug stored in the storage space 110 may pass through the first accommodation portion 120 so as to be discharged to the outside of the body 100 through the outlet 124.

The rear rotational magnet 220 may be located in the second accommodation portion 130. The rear rotational magnet 220 may have the same shape as the front rotational magnet 210. In detail, the rear rotational magnet 220 may have a cylindrical shape, and may have a central axis 222 arranged in the second direction y. The rear rotational magnet 220 may have the N-pole and the S-pole making contact with each other with the central axis 222 interposed therebetween.

An outer diameter of the rear rotational magnet 220 may be smaller than an inner diameter of the second accommodation portion 130. In addition, a length of the rear rotational magnet 220 in the second direction y may be longer than a height of the second accommodation portion 130 in the third direction z. Accordingly, the rotation of the rear rotational magnet 220 about the axis in the first direction x may be limited while the rear rotational magnet 220 may be freely rotatable about the axis in the second direction y within the second accommodation portion 130.

The rear rotational magnet 220 may selectively rotate about an axis in one of the first direction x and the second direction y under the control of an external magnetic field. For example, when the rear rotational magnet 220 rotates about the axis in the first direction x, the body 100 may rotate together with the rear rotational magnet 220 about the axis in the first direction x. In another example, when the rear rotational magnet 220 rotates about the axis in the second direction y, the rear rotational magnet 220 may open or close the second communication hole 132 by a magnetic force in association with the third fixed magnet 330 and the fourth fixed magnet 340.

The first fixed magnet 310 may be fixedly coupled to one side of the body 100 at a rear of the front rotational magnet 210. According to the embodiment, a groove may be formed at the one side of the body 100, and the first fixed magnet 310 may be fixedly coupled to the groove.

In the first fixed magnet 310, one of the N-pole and the S-pole may be adjacent to the front rotational magnet 210, and the other may be located farther than the previous one. The polarity of the first fixed magnet 310 adjacent to the front rotational magnet 210 may transmit the magnetic force to the front rotational magnet 210.

The second fixed magnet 320 may be fixedly coupled to an opposite side of the body 100 at the rear of the front rotational magnet 210. In detail, the second fixed magnet 320 may be arranged such that mutually different polarities of the first and second fixed magnets 310 and 320 face each other with the storage space 110 interposed therebetween. Therefore, due to the magnetic force acting between the polarity of the first fixed magnet 310 and the polarity of the second fixed magnet 320, the external magnetic field may not significantly affect between the first fixed magnet 310 and the second fixed magnet 320. The polarity of the second fixed magnet 320 adjacent to the front rotational magnet 210 may transmit the magnetic force to the front rotational magnet 210.

Due to the arrangement of the first and second fixed magnets 310 and 320 described above, mutually different polarities of the first and second fixed magnets 310 and 320 may apply magnetic forces to the front rotational magnet 210. In addition, the first fixed magnet 310 may apply the magnetic force to one pole of the front rotational magnet 210, and the second fixed magnet 320 may apply the magnetic force to the other pole of the front rotational magnet 210. Accordingly, forces generated between the first and second fixed magnets 310 and 320 and the front rotational magnet 210 may be the same forces, which are attractive forces or repulsive forces.

The third fixed magnet 330 may be fixedly coupled to one side of the body 100 at a front of the rear rotational magnet 210. According to the embodiment, a groove may be formed at the one side of the body 100, and the third fixed magnet 330 may be fixedly coupled to the groove.

In the third fixed magnet 330, one of the N-pole and the S-pole may be adjacent to the rear rotational magnet 220, and the other may be located farther than the previous one. The polarity of the third fixed magnet 330 adjacent to the rear rotational magnet 220 may transmit the magnetic force to the rear rotational magnet 220.

The fourth fixed magnet 340 may be fixedly coupled to an opposite side of the body 100 at the front of the rear rotational magnet 220. In detail, the fourth fixed magnet 340 may be arranged such that mutually different polarities of the third and fourth fixed magnets 330 and 340 face each other with the storage space 110 interposed therebetween. Therefore, due to the magnetic force acting between the polarity of the third fixed magnet 330 and the polarity of the fourth fixed magnet 340, the external magnetic field may not significantly affect between the third fixed magnet 330 and the fourth fixed magnet 340. The polarity of the fourth fixed magnet 340 adjacent to the rear rotational magnet 220 may transmit the magnetic force to the rear rotational magnet 220.

Due to the arrangement of the third and fourth fixed magnets 330 and 340 described above, mutually different polarities of the third and fourth fixed magnets 330 and 340 may apply magnetic forces to the rear rotational magnet 220. In addition, the third fixed magnet 330 may apply the magnetic force to one pole of the rear rotational magnet 220, and the fourth fixed magnet 340 may apply the magnetic force to the other pole of the rear rotational magnet 220. Accordingly, forces generated between the third and fourth fixed magnets 330 and 340 and the rear rotational magnet 220 may be the same forces, which are the attractive forces or the repulsive forces.

A magnetic torque may be formed by the control of the external magnetic field. The magnetic torque may include a first magnetic torque having an axis in the first direction x and a second magnetic torque having an axis in the second direction y.

When the first magnetic torque is formed, the front rotational magnet 210 and the rear rotational magnet 220 may rotate about the axis in the first direction x. The front rotational magnet 210 and the rear rotational magnet 220 may rotate together with the body 100 about the axis in the first direction x due to spatial constraints of the first accommodation portion 120 and the second accommodation portion 130. Through such rotation of the body 100, the drug delivery robot may perform moving and drilling operations.

When the second magnetic torque is formed, each of the front rotational magnet 210 and the rear rotational magnet 220 may rotate about the axis in the second direction y. Since the front rotational magnet 210 and the rear rotational magnet 220 have the outer diameters smaller than the first accommodation portion 120 and the second accommodation portion 130, respectively, the front rotational magnet 210 and the rear rotational magnet 220 may rotate independently within the first accommodation portion 120 and the second accommodation portion 130.

While the front rotational magnet 210 rotates about the axis in the second direction y, the attractive force and the repulsive force may be sequentially and repeatedly generated between the front rotational magnet 210 and the first and second fixed magnets 310 and 320. In detail, the attractive force and the repulsive force may be generated once for each rotation of the front rotational magnet 210. The attractive force acts as a force for pulling the front rotational magnet 210 toward the first and second fixed magnets 310 and 320, whereby the front rotational magnet 210 may close the first communication hole 122. In addition, the repulsive force acts as a force for pushing the front rotational magnet 210 in a direction away from the first and second fixed magnets 310 and 320, whereby the first communication hole 122 may be opened.

While the rear rotational magnet 220 rotates about the axis in the second direction y, the attractive force and the repulsive force may be sequentially and repeatedly generated between the rear rotational magnet 220 and the third and fourth fixed magnets 330 and 340. In detail, the attractive force and the repulsive force may be generated once for each rotation of the rear rotational magnet 220. The attractive force acts as a force for pulling the rear rotational magnet 220 toward the third and fourth fixed magnets 330 and 340, whereby the rear rotational magnet 220 may close the second communication hole 132. In addition, the repulsive force acts as a force for pushing the rear rotational magnet 220 in a direction away from the third and fourth fixed magnets 330 and 340, whereby the second communication hole 132 may be opened.

The external magnetic field may selectively form the first magnetic torque and the second magnetic torque. The first magnetic torque may be formed during the movement and drilling of the drug delivery robot, and the second magnetic torque may be formed during the drug delivery.

During the movement of the drug delivery robot, the front rotational magnet 210 and the rear rotational magnet 220 do not rotate about the axis in the second direction y, so that the first and second communication holes 122 and 132 may be closed by the attractive force in association with the first to fourth fixed magnets 310, 320, 330, and 340. Accordingly, in the drug delivery robot, the drug may be prevented from leaking to the outside during a moving process.

In addition, during the drug delivery, since the first and second communication holes 122 and 132 are opened as the front rotational magnet 210 and the rear rotational magnet 220 rotate about the axis in the second direction y, an amount of the discharged drug may be precisely adjusted by controlling the number of rotations of the front rotational magnet 210 and the rear rotational magnet 220.

Regarding the above technical content, the driving principle configured by the plurality of magnets of the drug delivery robot may be described through Mathematical formulas 1 to 6 below.

The magnetic torque applied by the external magnetic field will be calculated through Mathematical formula 1 below, and a rotating magnetic field applied to the front rotational magnet 210 and the rear rotational magnet 220 by the external magnetic field will be calculated through Mathematical formula 2 below.

$$T_e = m \times B_e \qquad \text{[Mathematical formula 1]}$$

(where $T_e$ is a torque applied to the magnet by the external magnetic field, and m is a magnetic moment)

$$B_e(t) = B_0(\cos(2\pi ft)U + \sin(2\pi ft)N \times U) \qquad \text{[Mathematical formula 2]}$$

(where $B_0$ is the intensity of a magnetic field, f is a rotational frequency, N is a unit vector of a rotation axis, and U is a unit vector perpendicular to the rotation axis)

When a unit vector N of the rotation axis of the rotating magnetic field is generated in the first direction x, the front rotational magnet 210 and the rear rotational magnet 220 may rotate about the axis in the first direction x, and the body 100 may rotate together with the front rotational magnet 210 and the rear rotational magnet 220 about the axis in the first direction x. Accordingly, the drug delivery robot may move and perform the drilling.

When no external magnetic field is applied, since the magnetic field generated by the first to fourth fixed magnets 310, 320, 330, and 340 may align the front rotational magnet 210 and the rear rotational magnet 220 such that θ (see FIG. 6 which will be described below) of the front rotational magnet 210 and the rear rotational magnet 220 is 90°, the attractive force is generated between the front rotational magnet 210 and the first and second fixed magnets 310 and 320 and between the rear rotational magnet 220 and the third and fourth fixed magnets 330 and 340, so that the first and second communication holes 122 and 132 may be closed.

When assuming the plurality of magnets as magnetic dipoles, a force generated in dipole b of the front rotational magnet 210 and the rear rotational magnet 220 by dipole a of the first to fourth fixed magnets 310, 320, 330, and 340 may be calculated by Mathematical formula 3 below.

$$F_{ab} = \frac{3\mu_0}{4\pi r^4}((r \times m_a) \times m_b + (r \times m_b) \times m_a - 2r(\Box_a \cdot m_b) + 5r((r \times m_a) \cdot (r \times m_b))) \qquad \text{[Mathmatical formula 3]}$$

(where $\mu_0$ is the magnetic permeability in air, r is a vector from dipole a to dipole b, r is a magnitude of the vector, $m_a$ is a magnetic moment of dipole a, and $m_b$ is a magnetic moment of dipole b)

Due to the attractive force between the front rotational magnet 210 and the first and second fixed magnets 310 and 320 and between the rear rotational magnet 220 and the third and fourth fixed magnets 330 and 340, which is calculated through the above mathematical formula 3, the front rotational magnet 210 and the rear rotational magnet 220 may close the first and second communication holes 122 and 132.

In this case, the attractive force and the repulsive force generated between the magnets may be determined by a rotation angle of the front rotational magnet 210 and the rear rotational magnet 220, and the rotation angle may be determined by a torque that is generated by the magnetic field generated by the first to fourth fixed magnets 310, 320, 330, and 340.

The magnetic field generated by the first to fourth fixed magnets 310, 320, 330, and 340 may be calculated as a magnetic field generated by dipole a and dipole b through Mathematical formulas 4 and 5 below.

$$T_{ab} = \Box_b + B_a \qquad \text{[Mathematical formula 4]}$$

(where $T_{ab}$ is a magnetic field torque generated by dipoles a and b, and $m_b$ is the magnetic moment of dipole b)

$$B_a = \frac{\mu_0}{4\pi}\left(\frac{3r(m_a \cdot r)}{r^5} - \frac{m_a}{r^3}\right) \qquad \text{[Mathmatical formula 5]}$$

(where $\mu_0$ is the magnetic permeability in air, r is a vector from dipole a to dipole b, r is a magnitude of the vector, and $m_a$ is a magnetic moment of dipole a)

Since the magnetic field generated by the first to fourth fixed magnets 310, 320, 330, and 340 align the front rotational magnet 210 and the rear rotational magnet 220 at 90°, the drug may be sealed in the storage space 110. When the front rotational magnet 210 and the rear rotational magnet 220 rotate, the fluid moves together due to a viscous force, so that the drug may be discharged from the storage space 110 to the outside of the body 110.

Figure 3:
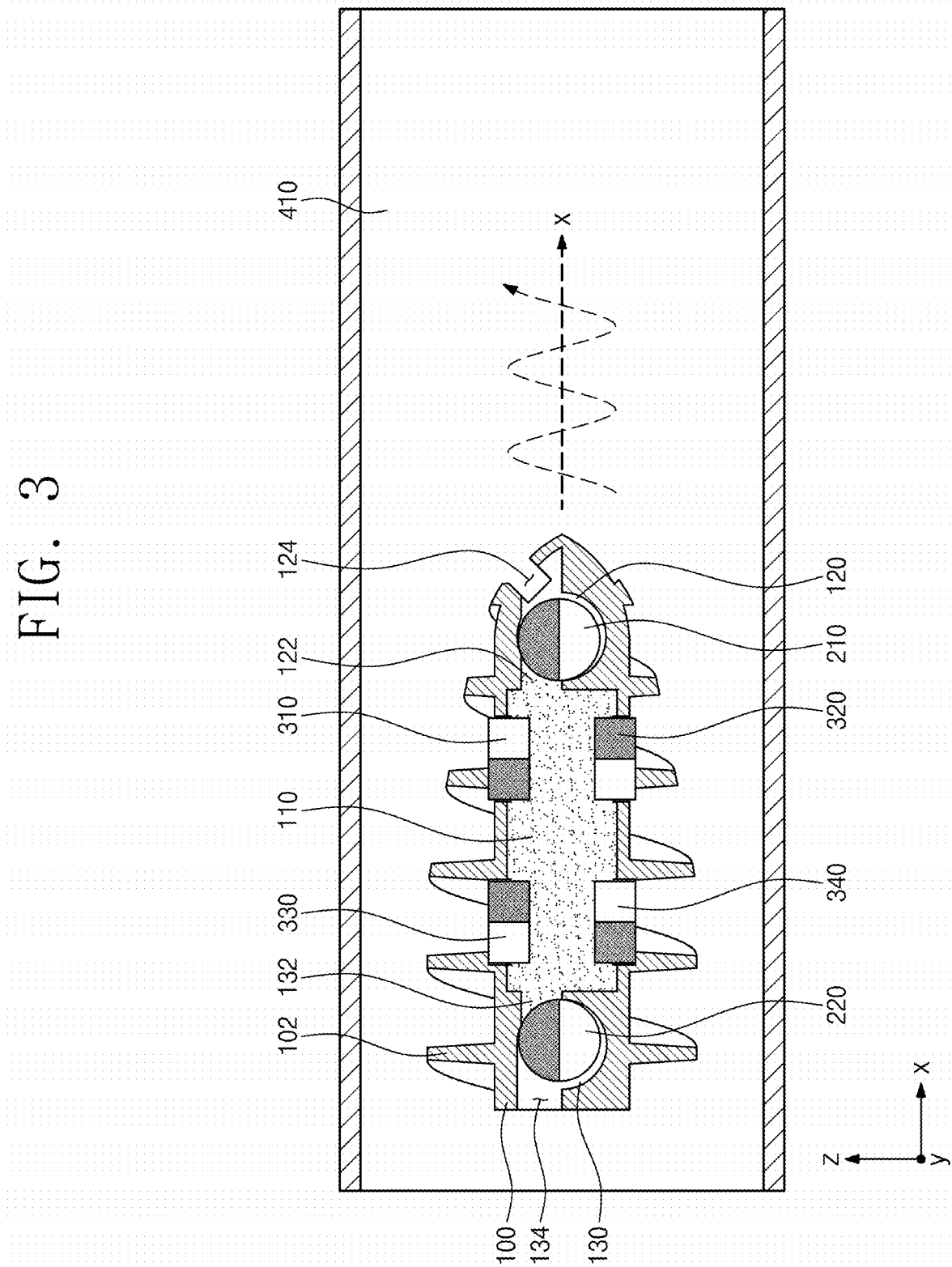
FIG. 3 is a view for describing a movement of the drug delivery robot according to the embodiment of the present invention.

FIG. 3 is a view for describing a movement of the drug delivery robot according to the embodiment of the present invention.

Referring to FIG. 3, when the rotating magnetic field is formed about the axis in the first direction x from the outside, the front rotational magnet 210 and the rear rotational magnet 220 may rotate about the axis in the first direction x, so hat the body 100 may also rotate about the axis in the first direction x. As the body 100 rotates about the axis in the first direction x, the body 100 may move in the first direction x.

Figure 4:
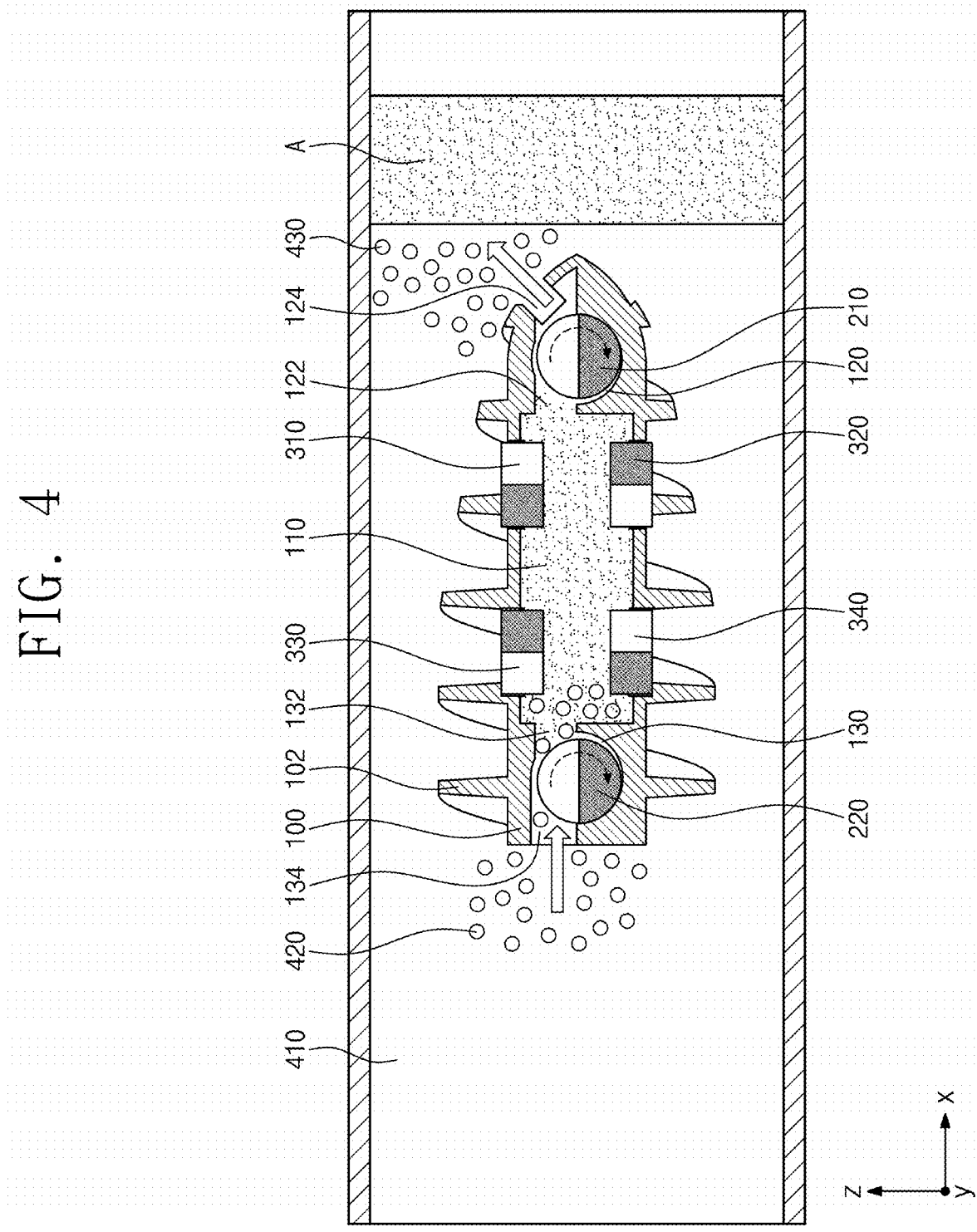
FIG. 4 is a view for describing drug delivery of the drug delivery robot according to the embodiment of the present invention.

FIG. 4 is a view for describing drug delivery of the drug delivery robot according to the embodiment of the present invention.

Referring to FIG. 4, when the drug delivery robot reaches a stenosis portion A during the movement while rotating about the axis in the first direction x, the generation of the rotating magnetic field about the axis in the first direction x may be stopped from the outside, and the rotating magnetic field about the axis in the second direction y may be formed. When the rotating magnetic field about the axis in the second direction y is formed, the front rotational magnet 210 and the rear rotational magnet 220 may rotate about the axis in the second direction y, and the first and second communication holes 122 and 132 may be opened or closed. As the first and second communication holes 122 and 132 are opened, a drug 430 stored in the storage space 110 may pass through the first communication hole 122 and the first accommodation portion 120 and may be discharged to the outside through the outlet 124, and the discharged drug 430 may soften the stenosis portion A. At this time, external blood 420 is introduced into the storage space 110 through the second communication hole 132, and the introduced external blood 420 may fill an empty space in the storage space 110, which is generated due to the discharge of the drug 430. The inflow of the external blood 420 acts as a force for pushing the drug 430 in the storage space 110 toward the first communication hole 122, so that the drug 430 may be smoothly discharged to the outside.

Figure 5:
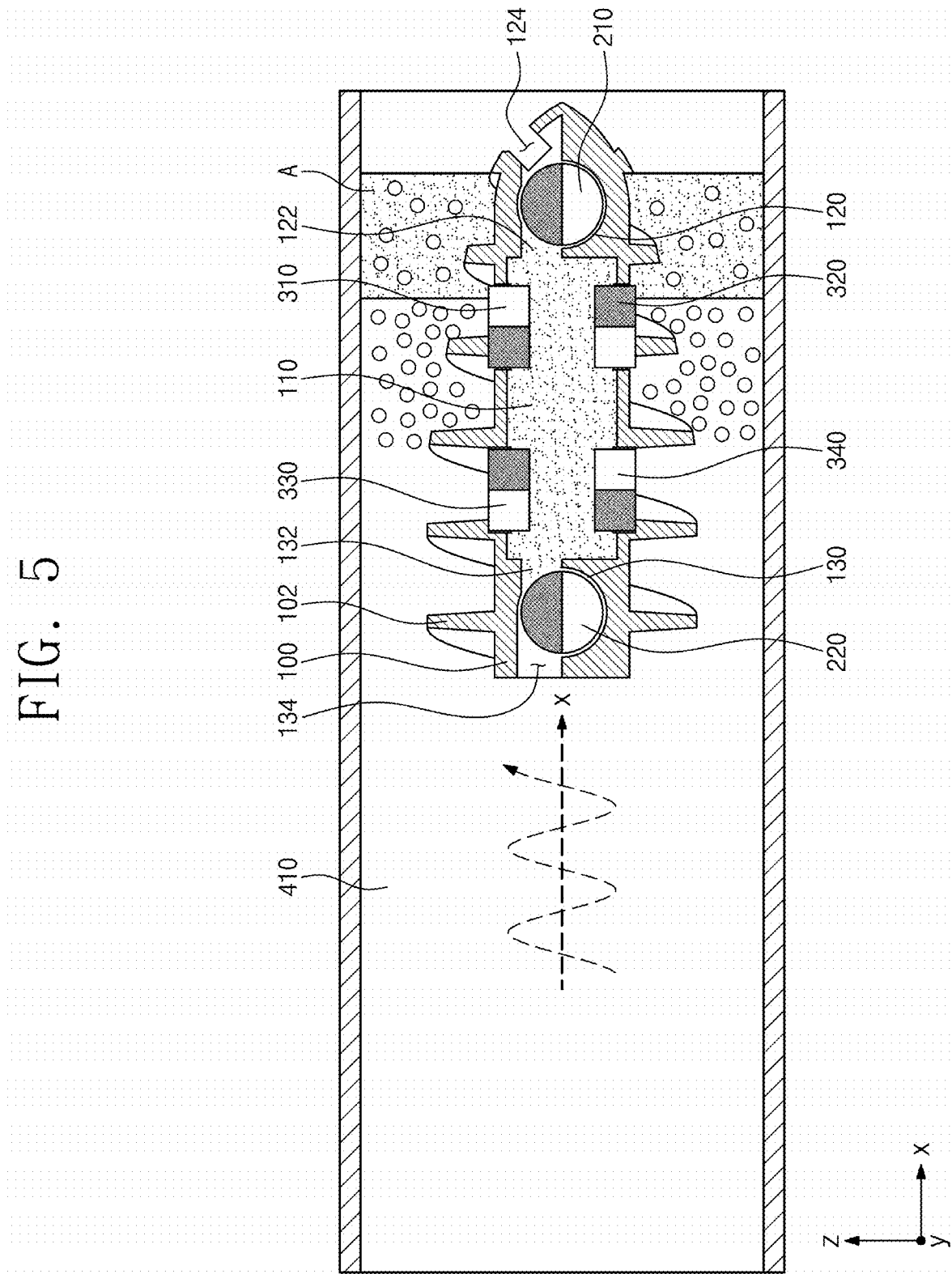
FIG. 5 is a view for describing drilling of the drug delivery robot according to the embodiment of the present invention.

FIG. 5 is a view for describing drilling of the drug delivery robot according to the embodiment of the present invention.

Referring to FIG. 5, when the discharge of the drug 430 stored in the storage space 110 is completed, the generation of the rotating magnetic field about the axis in the second direction y may be stopped from the outside, and the rotating magnetic field about the axis in the first direction x may be formed. The front rotational magnet 210, the rear rotational magnet 220, and the body 100 may move in the first direction x while rotating about the axis in the first direction x. The drug delivery robot may perform the drilling on the stenosis portion A softened by the drug 430. As the body 100 rotates about the axis in the first direction x, the body 100 may move in the first direction x.

Figure 6:
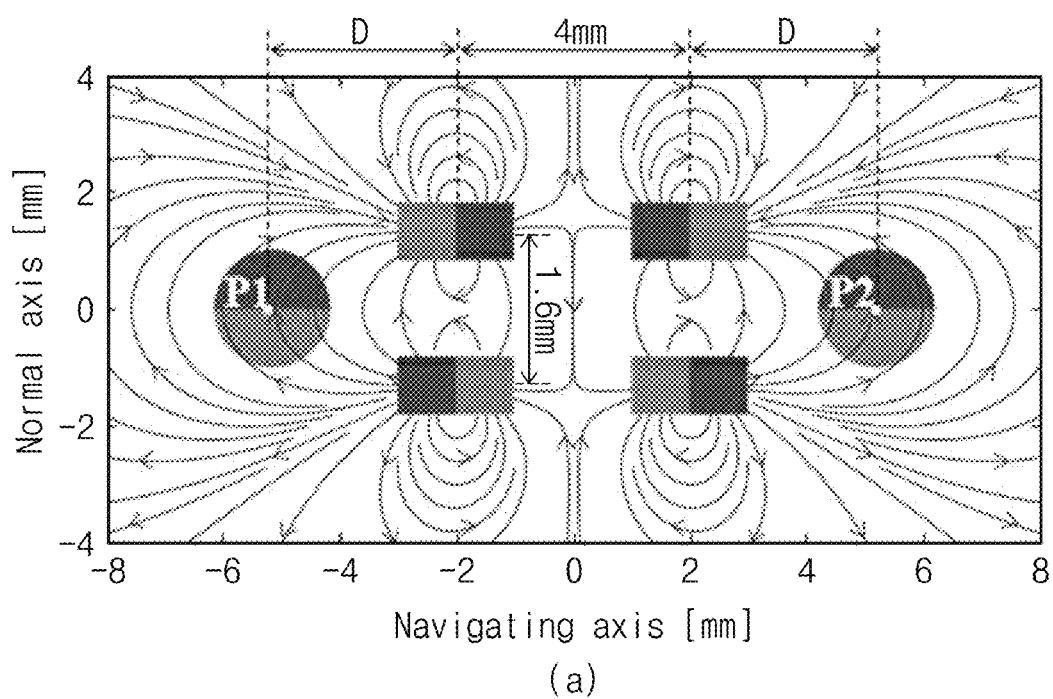
FIG. 6 is a view for describing a magnetic force between magnets included in the drug delivery robot according to the embodiment of the present invention.
Figure 6:
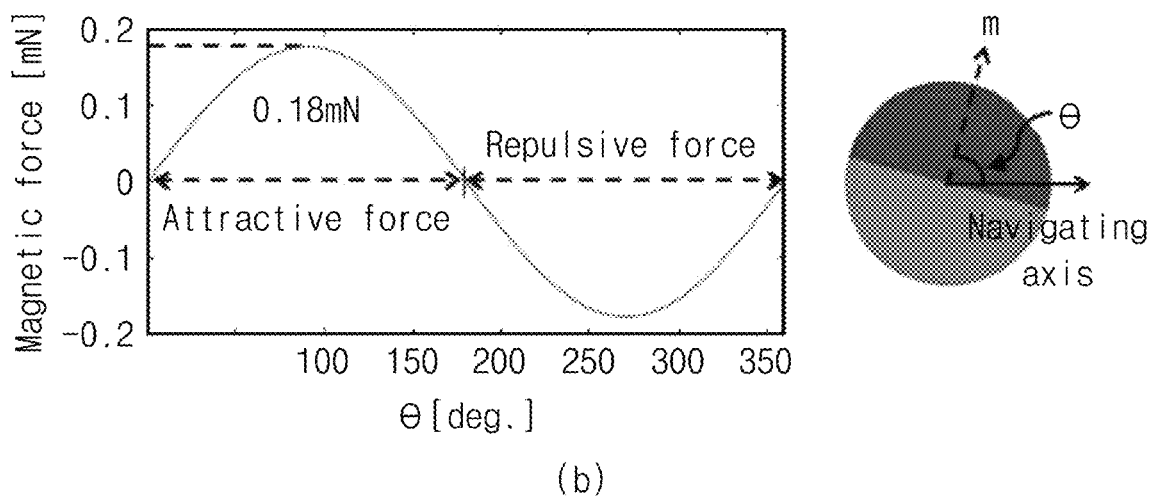

FIG. 6 is a view for describing a magnetic force between magnets included in the drug delivery robot according to the embodiment of the present invention.

Referring to (a) of FIG. 6, the magnetic field generated by the first to fourth fixed magnets may be observed. In this case, a distance between the first fixed magnet and the third fixed magnet and a distance between the second fixed magnet and the fourth fixed magnet may be 4 mm, and a distance between the first fixed magnet and the third fixed magnet and a distance between the second fixed magnet and the fourth fixed magnet may be 1.6 mm.

Referring to (b) of FIG. 6, the attractive and repulsive forces between the front rotational magnet and the first and second fixed magnets and the attractive and repulsive forces between the rear rotational magnet and the third and fourth fixed magnets, which are generated by the rotation of the front and rear rotational magnets, may be observed.

Although the exemplary embodiments of the present invention have been described in detail as described above, the scope of the present invention is not limited to a specific embodiment, and should be interpreted by the appended claims. Further, it should be understood by those skilled in the art to which the invention pertains that various changes and modifications can be made without departing from the scope of the present invention.

INDUSTRIAL APPLICABILITY

The drug delivery robot according to the present invention may be applied to medical activities of delivering a drug by moving along tubular organs in a human body.

The invention claimed is:

1. A drug delivery robot comprising:
a body including a storage space in which a drug is stored, a first accommodation portion formed at a front of the storage space in a first direction, an outlet which allows the first accommodation portion to communicate with an outside, and a first communication hole which allows the storage space to communicate with the first accommodation portion;
a front rotational magnet located in the first accommodation portion and having a central axis arranged in a second direction perpendicular to the first direction;
a first fixed magnet fixedly coupled to one side of the body at a rear of the front rotational magnet; and
a second fixed magnet fixedly coupled to an opposite side of the body with the storage space interposed between the first fixed magnet and the second fixed magnet, and arranged such that mutually different polarities of the first and second fixed magnets face each other,
wherein the front rotational magnet is able to selectively rotate about an axis in one of the first direction and the second direction under a control of an external magnetic field,
the body rotates together with the front rotational magnet about the axis in the first direction when the front rotational magnet rotates about the axis in the first direction, and
the front rotational magnet opens or closes the first communication hole by a magnetic force in association with the first fixed magnet and the second fixed magnet when the front rotational magnet rotates about the axis in the second direction.

2. The drug delivery robot of claim 1, wherein the front rotational magnet has a cylindrical shape, and has an N-pole and an S-pole making contact with each other with the central axis interposed therebetween.

3. The drug delivery robot of claim 2, wherein the first fixed magnet applies a magnetic force to one of the N-pole and the S-pole of the front rotational magnet, and
the second fixed magnet applies a magnetic force to a remaining one of the N-pole and the S-pole of the front rotational magnet.

4. The drug delivery robot of claim 1, wherein the rotation of the front rotational magnet about the axis in the first direction is limited while the front rotational magnet is freely rotatable about the axis in the second direction within the first accommodation portion.

5. The drug delivery robot of claim 1, wherein an inner diameter of the first accommodation portion is larger than an outer diameter of the front rotational magnet.

6. The drug delivery robot of claim 1, wherein the body is provided along an outer circumferential surface thereof with a protrusion having a spiral shape.

7. The drug delivery robot of claim 1, wherein the body includes a second accommodation portion formed at a rear of the storage space in the first direction, an inlet which allows the second accommodation portion to communicate with the outside, and a second communication hole which allows the storage space to communicate with the second accommodation portion, the drug delivery robot further comprises:
a rear rotational magnet located in the second accommodation portion and having a central axis arranged in the second direction perpendicular to the first direction;
a third fixed magnet fixedly coupled to the one side of the body at a front of the rear rotational magnet; and
a fourth fixed magnet fixedly coupled to the opposite side of the body with the storage space interposed between the third fixed magnet and the fourth fixed magnet, and arranged such that mutually different polarities of the third and fourth fixed magnets face each other,
the rear rotational magnet is able to selectively rotate about the axis in one of the first direction and the second direction under the control of the external magnetic field,
the body rotates together with the rear rotational magnet about the axis in the first direction when the rear rotational magnet rotates about the axis in the first direction, and
the rear rotational magnet opens or closes the second communication hole by a magnetic force in association with the third fixed magnet and the fourth fixed magnet when the rear rotational magnet rotates about the axis in the second direction.

8. The drug delivery robot of claim 7, wherein the rear rotational magnet has a cylindrical shape, and has an N-pole and an S-pole making contact with each other with the central axis interposed therebetween.

9. The drug delivery robot of claim 7, wherein the third fixed magnet applies a magnetic force to one of the N-pole and the S-pole of the rear rotational magnet, and the second fixed magnet applies a magnetic force to a remaining one of the N-pole and the S-pole of the rear rotational magnet.

10. The drug delivery robot of claim 7, wherein an inner diameter of the second accommodation portion is larger than an outer diameter of the rear rotational magnet.

11. A drug delivery robot comprising:
a body including a storage space in which a drug is stored, a second accommodation portion formed at a rear of the storage space in a first direction, an inlet which allows the second accommodation portion to communicate with an outside, and a second communication hole which allows the storage space to communicate with the second accommodation portion;
a rear rotational magnet located in the second accommodation portion and having a central axis arranged in a second direction perpendicular to the first direction;
a third fixed magnet fixedly coupled to one side of the body at a front of the rear rotational magnet; and
a fourth fixed magnet fixedly coupled to an opposite side of the body with the storage space interposed between the third fixed magnet and the fourth fixed magnet, and arranged such that mutually different polarities of the third and fourth fixed magnets face each other,
wherein the rear rotational magnet is able to selectively rotate about an axis in one of the first direction and the second direction under a control of an external magnetic field,
the body rotates together with the rear rotational magnet about the axis in the first direction when the rear rotational magnet rotates about the axis in the first direction, and
the rear rotational magnet opens or closes the second communication hole by a magnetic force in association with the third fixed magnet and the fourth fixed magnet when the rear rotational magnet rotates about the axis in the second direction.

* * * * *